United States Patent
Arndt et al.

(10) Patent No.: US 7,004,370 B2
(45) Date of Patent: Feb. 28, 2006

(54) DEVICE AND METHOD FOR DETERMINING PARAMETERS OF A WELDING SYSTEM

(75) Inventors: Volker Arndt, Erbach (DE); Klaus Offterdinger, Stuttgart (DE); Walter Pasdzior, Bensheim (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/363,097

(22) PCT Filed: Aug. 31, 2001

(86) PCT No.: PCT/DE01/03413

§ 371 (c)(1),
(2), (4) Date: Jun. 12, 2003

(87) PCT Pub. No.: WO02/18088

PCT Pub. Date: Mar. 7, 2002

(65) Prior Publication Data

US 2004/0094517 A1    May 20, 2004

(30) Foreign Application Priority Data

Sep. 1, 2000  (DE) ............................... 100 43 070

(51) Int. Cl.
B23K 13/08   (2006.01)
B23K 31/12   (2006.01)
G01N 29/04   (2006.01)

(52) U.S. Cl. .................... 228/8; 228/102; 228/103; 228/104; 73/579; 73/582

(58) Field of Classification Search .............. 228/102, 228/103, 104, 110.1, 8–10; 73/579, 582, 73/583, 587, 588, 597, 602

See application file for complete search history.

(56) References Cited

U.S. PATENT DOCUMENTS

| 3,410,983 | A | * | 11/1968 | Deutsch et al. ............. 219/109 |
| 4,447,700 | A | | 5/1984 | Cohen |
| 5,144,592 | A | * | 9/1992 | Bonis ......................... 367/87 |
| 5,670,071 | A | * | 9/1997 | Ueyama et al. ........ 219/130.51 |

(Continued)

FOREIGN PATENT DOCUMENTS

DE    43 25 878 A    2/1994

(Continued)

OTHER PUBLICATIONS

Matsuyama, K.: "Recent Developments and Trends . . . ", Welding International, Welding Institute, Abington, GB, vol. 10, No. 9, 1996, pp. 743-747.

(Continued)

Primary Examiner—Lynne R. Edmondson
(74) Attorney, Agent, or Firm—Michael J. Striker

(57) ABSTRACT

The invention relates to a device and method for determining parameters of a welding system. According to the invention, a welding area (18, 21, 22) is subjected to the action of ultrasonic waves, preferably to the action of shear waves, by using an ultrasound source (14). During a first welding process (n1), a signal processing (30) determines a first ultrasonic permeability (Dn1) from a received ultrasonic signal (UE). During at least one subsequent welding process (n2), a second ultrasonic permeability (Dn2) is determined from an ultrasonic signal (UE) that is received during a renewed exposure of the welding area (18, 21, 22) to ultrasonic waves. A display (32) and/or a diagnostic function and/or a correction of control quantities of the welding system is/are carried out as a function of the at least two ultrasonic permeabilities (Dn1, Dn2).

8 Claims, 3 Drawing Sheets

U.S. PATENT DOCUMENTS

| | | | |
|---|---|---|---|
| 5,920,014 A * | 7/1999 | Waschkies | 73/597 |
| 6,613,169 B1 * | 9/2003 | Georgeson et al. | 156/64 |
| 6,684,706 B1 * | 2/2004 | Knight et al. | 73/623 |
| 2004/0107774 A1 * | 6/2004 | Arndt | 73/602 |

FOREIGN PATENT DOCUMENTS

| | | |
|---|---|---|
| EP | 0 284 177 A | 9/1988 |
| EP | 0284177 A1 * | 9/1988 |

OTHER PUBLICATIONS

Nishida Y et al: "In-Process Control in Resistance Welding", Welding International, Welding Institiute, Abington, GB, vol. 10, No. 09, 1996, PP. 748-752.

* cited by examiner

DEVICE AND METHOD FOR DETERMINING PARAMETERS OF A WELDING SYSTEM

BACKGROUND OF THE INVENTION

The invention is based on a device and a method for determining parameters of a welding system according to the general class of the independent claims.

A method for evaluating resistance-welded joints is made known in DE-A 43 25 878. In order to evaluate welding procedures on-line, the ultrasonic permeability of the welded joint is determined by acting upon it with distortional waves. To this end, the mean ultrasonic energy is determined—during each current half-wave of the welding current—from the output signal of the ultrasonic receiver within a time window that is delayed by a defined lag time as compared with the constant ultrasonic transmitted signal. Said mean ultrasonic energy is used as a measure of the quality of the welded joints. To regulate the welding process, the variation of the ultrasonic permeability can be compared with a prespecified sample trace in order to change the welding parameters, e.g., current intensity, accordingly if a deviation occurs, so that the subsequent ultrasonic permeability values can conform with the sample trace once more.

The object of the invention is to determine further parameters relevant for the welding procedure that provide an indication of the condition of the welding system. It is desirable, in particular, to determine the wear of an electrode of the welding system exactly so that it can be displayed or so that maintenance intervals for the electrodes can be stated automatically. It will also be made possible for the closed-loop control system to take the aging process of the welding electrode into account.

This object is attained by means of the features of the independent claims.

ADVANTAGES OF THE INVENTION

The device according to the invention for determining parameters of a welding system uses an ultrasonic source to act on a welded region with ultrasonic waves, preferably distortional waves. In a first welding procedure, a signal processing determines—based on a received ultrasonic signal—a measure of a first ultrasonic permeability of the welded region. It also determines—based on an ultrasonic signal received in a further welding procedure—a measure of a further ultrasonic permeability of the welded region. The measure of the first ultrasonic permeability and the further ultrasonic permeability are stored in order to trigger a display and/or a diagnostic function and/or to correct control variables of the welding system. It has been demonstrated that the measure of the ultrasonic permeability changes characteristically as the number of welding procedures increases. This is due to wearing of the electrodes and/or the electrode caps. As the duration of welding increases, the ultrasonic permeability of the welded region increases. This understanding is taken into consideration by storing at least two corresponding ultrasonic permeability values and performing a subsequent evaluation. It is therefore possible, according to the invention, to determine the condition of the electrodes and/or the electrode caps immediately during the on-going welding procedure based on the changing ultrasonic permeability. Maintenance and/or inspection intervals during which the condition of the electrodes is typically examined can therefore be eliminated.

In an advantageous further development, the ultrasonic permeability depending on the number of welds or a variable dependent thereon is compared with a limit value that, when exceeded, indicates to the operator that maintenance must be performed on the electrode and/or the electrode cap. For example, the electrode cap must be completely replaced or milled off. The welding device can therefore be monitored automatically by the signal detection. The device automatically indicates when the operator should intervene. Additionally, a control signal can be generated automatically with which an automatic maintenance function is activated. For example, an automatic milling system starts to mill the worn electrode caps and/or electrodes on its own. The production process can be further optimized by the fact that the maintenance function can be activated as needed.

The current regulation of the resistance-welding process can also be influenced based on the electrode wear curve. Preferably, as the number of welding processes increases, the current should be increased at the same rate as the increase in ultrasonic permeability. As a result, the current density through the welded region is kept constant, which contributes to consistent quality of the weld. This current adjustment can be carried out continuously, as a result of which a consistently high quality of the welds and the resultant welding spots is obtained automatically, even as the wear on the electrodes and/or electrode caps increases.

In an advantageous further development, the determined ultrasonic permeability values are subjected to a certain smoothing procedure to determine a trend characteristic based on said values. This ensures that individual data points do not mistakenly activate the maintenance display.

Additional advantageous further developments result from the further dependent claims and their description.

An exemplary embodiment of the invention is shown in the drawings and is described in greater detail below.

Figure 5A:
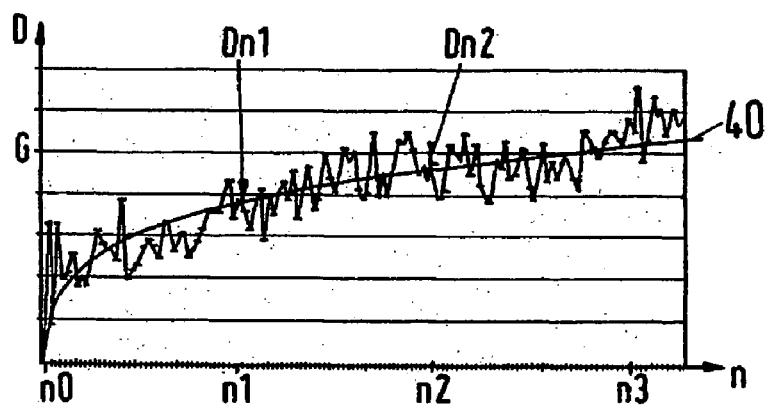
Figure 5B:
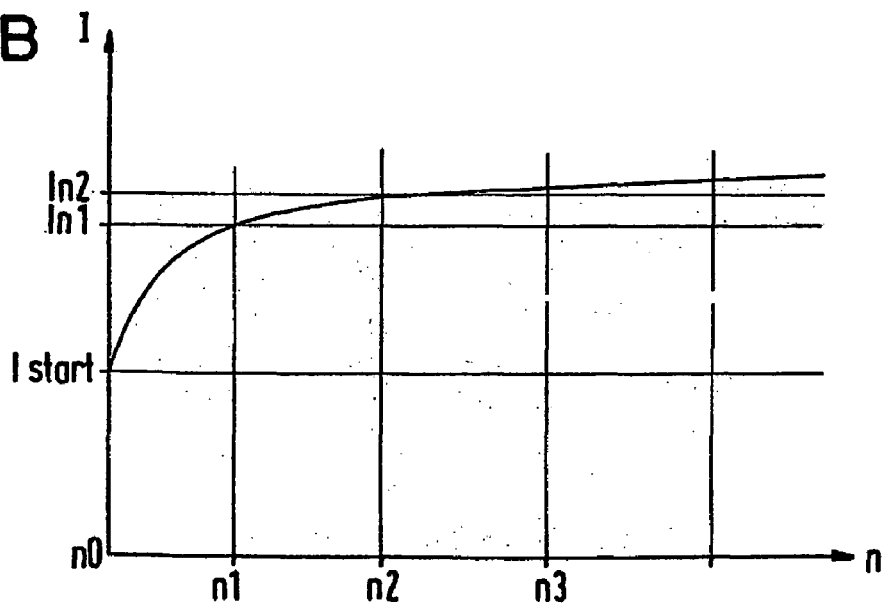
Figure 3A:
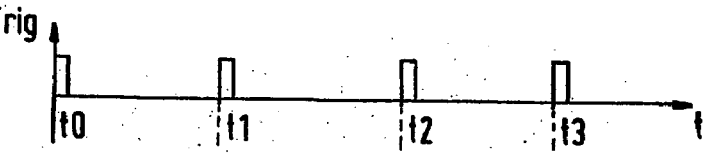
Figure 3B:
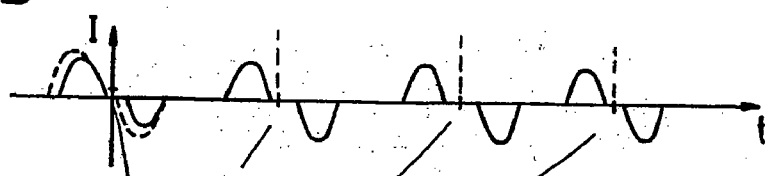
Figure 3C:
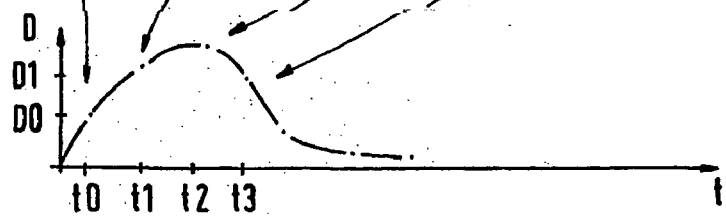
Figure 4:
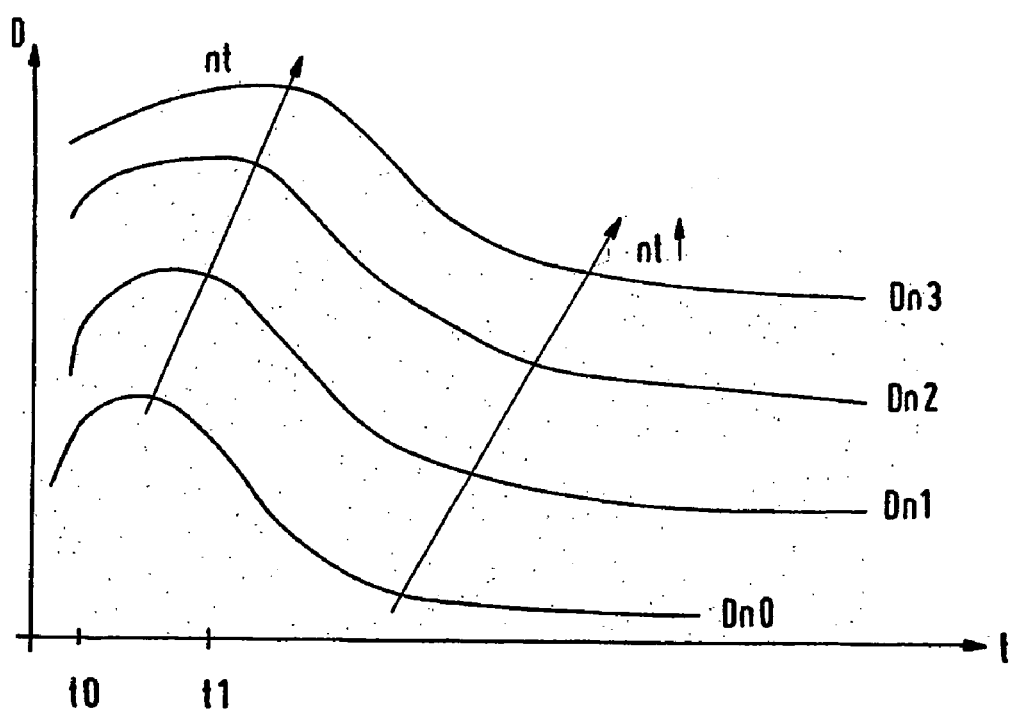

FIGS. 3a through 3c show the associated trigger and current variations with associated ultrasonic permeability, FIG. 4 shows the characteristic ultrasonic permeability variations as a functionn of the number of welding spots and/or welds, and FIGS. 5a and 5b show variations in ultrasonic permeability, the ultrasonic permeability trend characteristic, and the current as a function of the number of welds.

DESCRIPTION OF THE PREFERRED EMBODIMENTS

A first welding electrode 11 is acted upon by a current 1. An ultrasonic transmitter 14 is located at the first welding electrode 11. An ultrasonic receiver 18 is placed on the outer wall of a second welding electrode 12. A first electrode cap 19 is mounted on the end of the first welding electrode 11, and a second electrode cap 20 is mounted on the end of the second welding electrode 12. A first metal sheet 21 and a metal sheet 22 joined by a welding spot 18 are located between the two electrode caps 19, 20. The ultrasonic transmitter 14 is acted upon by a transmitted signal US furnished by a transmitter control 24 as a function of a trigger signal Trig from a welding control 28. The transmitted signal US is sent to the ultrasonic receiver 16 via the first electrode 11, the first electrode cap 19, the first and second metal sheet 21, 22, the welding spot 18, the second electrode cap 20, and via the second electrode 12.

The ultrasonic receiver 16 emits a measuring signal UE to a signal detection 26. The signal detection 26 forwards the detected measuring signal UE to a signal processing 30.

Figure 2A:
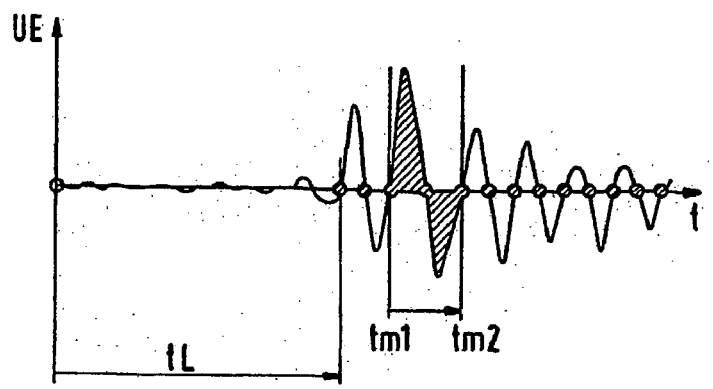
FIGS. 2a, 2b show the ultrasonic transmitted and received signals.
Figure 2B:

FIG. 2a shows the course of the measuring signal UE over time. At instant t0, the ultrasonic transmitter 14 emits a transmitted signal US that contains a sinusoidal vibration (FIG. 2b). After the transit time tl, the ultrasonic receiver 16 receives the measuring signal UE, the level of the amplitude of the sinusoidal vibration of which first increases and then decreases, and then dies away. The measuring signal UE is evaluated within a measuring window with the parameters TM1 and TM2.

In normal operation, the resistance-welding system is acted upon by a discontinuous current I comprising sinusoidal half-waves (FIG. 3b). As indicated using dotted lines, the current intensity I can be influenced by changing the control variable. The variation of the trigger signal Trig results depending on the current variation I according to FIG. 3b. The trigger signal Trig is selected so that a measurement is started by emission of the transmitted signal US at the moment when no current I flows. The ultrasonic permeability D is shown in FIG. 3c as a function of time t. For a good weld, the ultrasonic permeability curve D has the fluctuation shown. Only those measured values that lie within the time window TM1, TM2 contribute to the determination of the ultrasonic permeability D. The trigger signal Trig activates the emission of the transmitted signal US.

The ultrasonic permeability curve D according to FIG. 3c changes as the number n of welding spots and/or welds increases. The ultrasonic permeability D increases as the number n of welding spots increases, as shown in FIG. 4.

According to FIG. 5a, the measures for the ultrasonic permeability values Dn are plotted as a function of the number n of welds and/or welding spots. The trend characteristic 40 is determined using a mathematical smoothing procedure based on these measured values. The variation of the current I as a function of the number n of welding spots and/or welds essentially conforms with the trend characteristic 40, FIG. 5b.

According to the invention, the ultrasonic permeability D is now evaluated with different welding procedures to determine the wear of the electrodes 11, 12 or the electrode caps 19, 20. The ultrasonic permeability D increases as the duration of welding increases, and/or as the number of welds increases, due to flattening of the electrode caps 19, 20.

Figure 1:
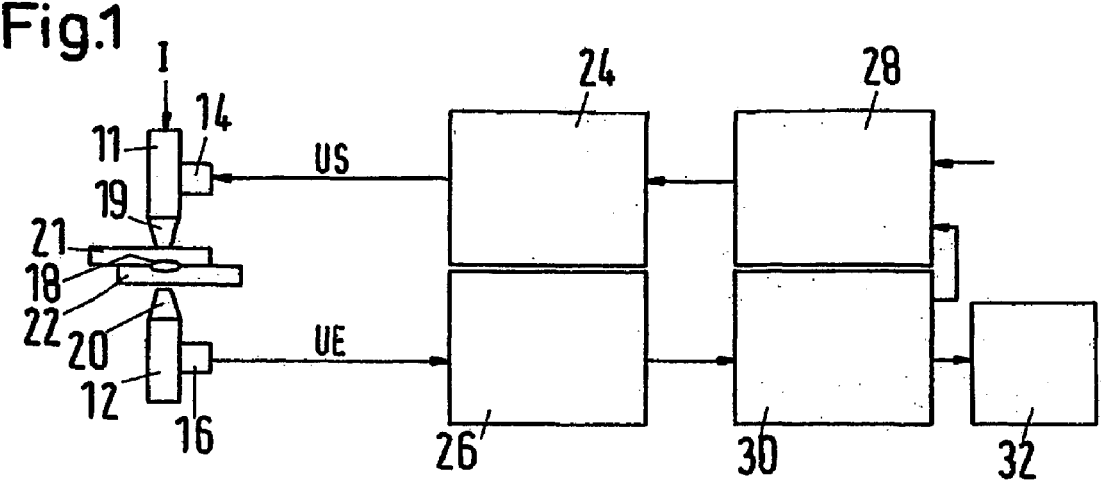
FIG. 1 is a block diagram of the device according to the invention.

The way in which the ultrasonic permeability curve D is determined for a weld will now be described with reference to FIGS. 1 through 3. The measuring procedure of the welding process starts at instant t0. At instant t0, the welding control 28 emits a trigger impulse Trigg to the transmitter control 24 which then triggers the ultrasonic transmitter 14 to emit the transmitted signal US shown in FIG. 2b. The ultrasonic transmitter 14 produces distortional waves, preferably transverse ultrasonic waves or torsional sound vibration. The signal US emitted by the transmitter 14 travels via the welded region 18, 21, 22 to the electrodes 11, 12, as well as the electrode caps 19, 20 to the ultrasonic receiver 16, which receives the measured signal UE and forwards it to signal detection 26. The signal variation of the measured signal UE is shown in FIG. 2a. Based on the measured signal UE, the signal detection 26 and the signal processing 30 determine the ultrasonic permeability D at the (trigger) instant t0. To determine the ultrasonic permeability D of the welded region during each current half-wave of the welding current, the mean ultrasonic energy of the measured signal UE is determined within a suitable time window TM1, TM2. A measure of the ultrasonic energy is the area enclosed by the measured signal UE, shown as shaded areas in FIG. 2a. The root-mean-square value or the arithmetic mean of the curve trace of the measured signal UE lying within the measurement window TM1, TM2, for example, could be calculated as a measure of the ultrasonic permeability D at instant t0. This is repeated for a single weld often enough to obtain the curve trace shown in FIG. 3c. The welded region 18, 21, 22 is acted upon by the current variation I shown in FIG. 3b. During this one welding procedure, the ultrasonic permeabilities are determined once more at instants t1, t2, t3, etc. using the method just described. When a trigger signal arrives, a transmitted signal US is emitted once more, as shown in FIG. 2b, which is followed by the ultrasonic permeability determination described in conjunction with FIG. 2a. For a proper spot weld, the characteristic variation of ultrasonic permeability shown in FIG. 3c therefore results. As the welded region melts further, the ultrasonic permeability D increases to a maximum value. If the welded region now becomes fluid, the distortional waves become weaker, so that the ultrasonic permeability decreases once more. Reference is made to DE-A 43 25 878 for a more detailed description.

The ultrasonic permeability curves Dn0, Dn1, Dn2, Dn3 plotted against the number of welds are now shown in FIG. 4. As the number n (n0<n1<n2<n3) of welds increases, the corresponding ultrasonic permeability amplitude also increases at matching instants t0, t1, when the number n of welds is carried out with the same electrode caps 19, 20 and/or electrodes 11, 12 subject to wear. Essentially, it is observed that the amplitude of the ultrasonic permeability curve D increases as the number n of welds increases, and it is observed that the maximum of the ultrasonic permeability curve D shifts.

This change in the ultrasonic permeability D as the number n of welds increases is therefore a measure of the wear of the electrode 11, 12 or the electrode caps 19, 20. Wearing electrode caps 19, 20 become increasingly wider as the number n of welds increases, which is why it is easier for the ultrasonic waves to pass through the welded region. This phenomenon can now be used in order to detect wear on the welding system and to implement suitable countermeasures.

Hereinbelow it will be assumed that a certain number n of welds, preferably spot welds, will be carried out with the same electrodes 11, 22 and the corresponding electrode caps 19, 20. A measure for the ultrasonic permeability D will be determined first. To this end, the associated ultrasonic permeability DnO(t0), Dn(t1) will be determined, for example, starting with the first weld n0 at a previously determined instant t0 or t1, as described above. This determination is also carried out with the subsequent welds n1, n2, n3 with the same electrode 11, 12 and/or the same electrode caps 19, 20 and, in fact, at the same instant t0, t1 as with the previous measurement. This results in measured values of ultrasonic permeability as shown in FIG. 5a. The measured values of ultrasonic permeability Dn determined in this fashion as a function of the number n of welds are now subjected to a smoothing procedure. This can be the method of least squares, for example, whereby a trend characteristic 40 results based on the formula $y = c\, x^b$ (y represents the trend characteristic, x is the ultrasonic permeability Dn, and c and b are certain process parameters). This trend characteristic 40 is also shown in FIG. 5a. Based on the trend characteristic 40, it is apparent that the ultrasonic permeability D increases slowly as a function of the number n of welds. An updated trend characteristic 40 is always determined based on the new measured values that keep coming.

In addition to this instant-based determination of a measure of the ultrasonic permeability Dn, the maximum of the respective ultrasonic permeability Dn could also be stored in order to determine the trend characteristic. The area enclosed by the respective permeability curve could also serve as a measure of the ultrasonic permeability Dn, which said area can be determined using certain mathematical methods. Another measure of the ultrasonic permeability Dn, for example, could be the four amplitudes of the ultrasonic permeability Dn(t0), Dn(t1), Dn(t2), Dn(t3) according to FIG. 3c, which said amplitudes are added or determined arithmetically, for example. The same method for determining a measure of the ultrasonic permeability should be used for each weld in order to ensure comparability of the measures of the ultrasonic permeabilities Dn as a function of the number n of welds. The trend characteristic 40 is then processed as described hereinabove.

This trend characteristic 40 is constantly compared with a specifiable limit value G. If the trend characteristic 40 exceeds the limit value G, this indicates that the electrodes 11, 12 and/or the electrode caps 19, 20 have a great deal of wear, and intervention is required. The signal processing 30 performs the appropriate processing of the ultrasonic permeability D and generates the trend characteristic 40. It triggers a display 32 accordingly. If the trend characteristic 40 exceeds the limit value G, a warning is activated. In this manner the operator is informed that the electrode caps 19, 20 or the electrodes 11, 12 must be replaced or handled in another fashion. For example, the electrode caps 19, 20 could be re-milled in order to use them for further welding procedures.

If the trend characteristic 40 exceeds the limit value G, the signal processing 30 generates a control signal. This control signal can be used, for example, to activate an automatic maintenance function. For instance, an automatic milling system starts the procedure to mill the worn electrode caps and/or electrodes. Automatic replacement of the electrodes or electrode caps could be activated as well. Control of such functions on an as-needed basis is therefore made possible.

In order to obtain consistent quality of the welds, the current density through the welded region 18, 21, 22 should be kept constant. Since the tips of the electrode caps 19, 20 become wider, the current density—given a constant current I—would drop as the number n of welds increases. Since statements regarding the wear of the electrode caps 19, 20 are now available in the form of the trend characteristic 40, however, the current I can be changed as a function of this trend characteristic 40. The current variation I should have a trace that is essentially parallel with the trend characteristic 40 in order to keep the current density constant in the welding region 18, 21, 22. To this end, the current I is adjusted accordingly.

If the new current In2 is reset for the number n2 of welds, for example, this could take place using the following equation: $In2 = F \times Dn2 / Dn1 \times In1$, whereby Dn1, Dn2 are the corresponding ultrasonic permeability values of the trend characteristic 40 for the respective number n1, n2 of welds, and In1 is the current value with which the system was acted upon at the number n1 of welds, and F is a proportionality factor. In this manner, the new current value to be set could be adjusted in steps.

What is claimed is:

1. A device for determining parameters of a welding system using an ultrasonic source (14) that acts on a welded region (18, 21, 22) with ultrasonic waves, comprising:

signal processing means (30) that in a welding procedure determines a measure for an ultrasonic permeability of the welded region (18, 21, 22) from a received ultrasonic signal (UE), wherein the signal processing means (30) is adapted for determining a trend characteristic (40), representing an ultrasonic permeability (D) as a function of a number of welds (n), based on ultrasonic permeability values (Dn0, Dn1, Dn2, Dn3) measured at different welds (n0, n1, n2, n3), and the signal processing means (30) is further adapted for generating a maintenance signal and/or adjusting a welding current (In1, In2) of the welding system based on said trend characteristic (40).

2. The device of claim 1, wherein the signal processing means (30) is adapted for determining the parameters of a mathematical function by using the method of least squares in order to determine said trend characteristic (40).

3. The device of claim 1, wherein comparison means (30) are provided that compare the trend characteristic (40) with a specifiable limit value (G) to generate said maintenance signal.

4. The device of claim 1, wherein a new welding current (In2) for a next weld (n2) is calculated so that a ratio of said new welding current (In2) and a welding current (In1) of a previous weld (n1) equals a ratio of values of said trend characteristic (40) for respective weld number (n2, n1) multiplied by a predetermined proport onality factor (F).

5. A method for determining parameters of a welding system using an ultrasonic source that acts on a welded region (18, 21, 22) with ultrasonic waves, comprising the steps of:

in a welding procedure, determining a measure for an ultrasonic permeability of the welded region (18, 21, 22) from a received ultrasonic signal (UE);

determining a trend characteristic (40), representing an ultrasonic permeability (D) as a function of a number of welds (n), based on ultrasonic permeability values (Dn0, Dn1, Dn2, Dn3) measured at different welds (n0, n1, n2, n3); and generating a maintenance signal and/or adjusting a welding current (In1, In2) of the welding system based on said trend characteristic (40).

6. The method of claim 5, wherein the step of determining said trend characteristic (40) comprises the step of determining parameters of a mathematical function by using the method of least squares.

7. The method of claim 5, further comprising the steps of comparing the trend characteristic (40) with a specifiable limit value (G) and generating said maintenance signal when said trend characteristic (40) exceeds said limit value (G).

8. The method of claim 5, wherein the step of adjusting said welding current (In1, In2) comprises the step of calculating a new welding current (In2) for a next weld (n2) so that a ratio of said new welding current (In2) and a welding current (In1) of a previous weld (n1) equals a ratio of values of said trend characteristic (40) for respective weld numbers (n2, n1) multiplied by a predetermined proportionality factor (F).

* * * * *